United States Patent
Stenberg

(10) Patent No.: US 8,309,789 B2
(45) Date of Patent: Nov. 13, 2012

(54) ABSORBENT ARTICLE

(75) Inventor: Anders Stenberg, Onsala (SE)

(73) Assignee: SCA Hygiene Products AB, Göteborg (SE)

( * ) Notice: Subject to any disclaimer, the term of this patent is extended or adjusted under 35 U.S.C. 154(b) by 710 days.

(21) Appl. No.: 09/879,151

(22) Filed: Jun. 13, 2001

(65) Prior Publication Data

US 2002/0016579 A1   Feb. 7, 2002

Related U.S. Application Data

(60) Provisional application No. 60/211,188, filed on Jun. 13, 2000.

(30) Foreign Application Priority Data

Jun. 13, 2000   (SE) ...................... 0002206

(51) Int. Cl.
*A61F 13/15* (2006.01)

(52) U.S. Cl. ...................................... 604/361

(58) Field of Classification Search .................. 604/361, 604/362
See application file for complete search history.

(56) References Cited

U.S. PATENT DOCUMENTS

| | | | |
|---|---|---|---|
| 3,952,746 A | 4/1976 | Summers | |
| 4,022,211 A | 5/1977 | Timmons et al. | |
| 4,192,311 A | 3/1980 | Felfoldi | |
| 4,231,370 A | 11/1980 | Mroz et al. | |
| 4,662,875 A | 5/1987 | Hirotsu et al. | |
| 4,738,674 A * | 4/1988 | Todd et al. | 5/484 |
| 5,354,289 A * | 10/1994 | Mitchell et al. | 604/358 |
| 5,531,731 A | 7/1996 | Brusky | |
| 5,766,212 A | 6/1998 | Jitoe et al. | |
| 5,839,585 A * | 11/1998 | Miller | 211/49.1 |
| 5,902,296 A * | 5/1999 | Fluyeras | 604/361 |
| 5,947,943 A * | 9/1999 | Lee | 604/361 |
| 6,030,373 A | 2/2000 | Van Gompel et al. | |
| 6,059,710 A * | 5/2000 | Rajala et al. | 493/346 |
| 6,307,119 B1 * | 10/2001 | Cammarota et al. | 604/361 |

(Continued)

FOREIGN PATENT DOCUMENTS

CA   2256049   6/1999

(Continued)

OTHER PUBLICATIONS

Opposition filed in a corresponding EP application, Oct. 20, 2005.

(Continued)

*Primary Examiner* — Lynne Anderson
(74) *Attorney, Agent, or Firm* — Buchanan Ingersoll & Rooney PC

(57) ABSTRACT

Absorbent article such as a diaper and incontinence guard, in which on the inside of the liquid impervious backsheet (3), i e on the side adjacent the absorbent body, there is arranged a wetness indicator (9) in a certain pattern, which is visible through the backsheet material. The wetness indicator (9) is applied on or adjacent at least one strip (10) having a color or tint different from the rest of the backsheet material (3). The color or tint of the strip (10) can also be an indication of the product type, size absorption capacity or the like of the article. Moreover there can on the strip (10) be printed symbols (11), codes or the like indicating product type or the like.

20 Claims, 3 Drawing Sheets

U.S. PATENT DOCUMENTS 6,747,185 B2     6/2004    Inoue et al.

FOREIGN PATENT DOCUMENTS

| | | |
|---|---|---|
| EP | 0 203 715 | 12/1986 |
| EP | 0 211 524 | 2/1987 |
| EP | 0496567 A2 | 7/1992 |
| EP | 0 925 769 | 6/1999 |
| EP | 0951889 A1 | 10/1999 |
| FR | 2 711 317 | 4/1995 |
| GB | 2 327 354 | 1/1999 |
| JP | S59-024704 | 2/1984 |
| JP | H10-075980 | 3/1998 |
| RU | 2145830 | 2/2000 |
| WO | 95/00099 | 1/1995 |
| WO | 99/16401 | 4/1999 |

OTHER PUBLICATIONS

Translation of Colombian Office Action issued in a corresponding application, Aug. 10, 2004.

Opposition information filed in a corresponding EP application, Jun. 11, 2007.

* cited by examiner

ABSORBENT ARTICLE

This application claims priority under 35 U.S.C. §§119 and/or 365 to SE 0002206-1 filed in Sweden on Jun. 13, 2000 and to U.S. 60/211,188 filed in the United States on Jun. 13, 2000; the entire content of which is hereby incorporated by reference.

TECHNICAL FIELD

The present invention refers to an absorbent article such as a diaper or incontinence guard comprising a liquid pervious topsheet, a liquid impervious backsheet and an absorbent body enclosed therebetween, at which on the inside of the liquid impervious backsheet, i e on the side adjacent the absorbent body, there is arranged a wetness indicator in a certain pattern, which is visible through the backsheet material.

BACKGROUND OF THE INVENTION

Wetness indicators especially on diapers and incontinence guards for adult incontinent persons, have been known for several years and facilitates for the nursing staff to determine whether the diaper or incontinence guard needs to be changed. It for example known through EP-A-0 211 524 to print a pattern of a water soluble dye on the inside of the backsheet material of a diaper by means of ink beam technique. The dyestuff can alternatively be of a type that changes colour or tint when brought into contact with urine. The printed pattern can also consist of symbols or codes for quality- or other manufacturing control.

It is further known through EP-A-0 203 715 to treat an absorbent body of a diaper so that it gets a tight paperlike structure on the backside, which then is used as a reception surface for a wetness indicating dye applied in a pattern that is visible through the backside material of the diaper.

It is also known to have capillary wetness indicators, i e a thin strip or thread having a high capillary effect arranged in connection to the absorption body and which is in contact with an indicator which dissolves, changes colour or tint when brought in contact with a liquid. Such wetness indicators are known through for example U.S. Pat. No. 4,738,674 and GB-A-2 327 354.

The wetness indicator can be arranged at different locations, such as along the side of the absorption body or on the underside thereof. It can be therefore be difficult for the nurse to locate the wetness indicator on the article in order to read it to see whether the article needs to be changed or not.

WO 99/16401 discloses an diaper having a wetness indicator on the inside of the backsheet material. The backsheet material is a laminate of a fibrous nonwoven material and a polymer sheet. A plurality of translucent windows are arranged in said backsheet through which the wetness indicator is visible.

U.S. Pat. No. 4,231,370 discloses a diaper having a wetness indicator in the form of a coating applied in a pattern on the inside of a translucent backsheet material.

FR-A-2 711 317 discloses a wetness indicator comprising an inner portion which changes colour when it is wetted by urine and an outer portion which is translucent plastic material.

EP-A-0 925 769 discloses a diaper having a backsheet with transparent zones through which a wetness of the absorbent core can be observed.

OBJECT AND MOST IMPORTANT FEATURES OF THE INVENTION

The object of the present invention is to make it easier for the nurse to identify the location of the wetness indicator on the article and by that facilitate the reading thereof. This has been solved by applying the wetness indicator on or adjacent at least one strip having a colour or tint different from the rest of the backsheet material.

According to one embodiment the strip is separate from the backsheet material and is applied to the inside thereof.

According to another embodiment the strip is a part of the backsheet material which is coloured in another colour or tint than the rest of the backsheet material.

According to a preferred embodiment of the invention the colour or tint of the strip is an indication of the type, size, absorption capacity or the like of the article.

According to an embodiment the strip extends in the longitudinal direction of the article over the entire or at least over a substantial part thereof.

According to another embodiment the strip extends in the transverse direction of the article and is applied opposite the part of the article that is intended to form a fold in the folded packaging position of the article.

The width of the strip should be between 1 and 8 cm, preferably between 2 and 7 cm and more preferably between 3 and 6 cm.

On the strip or adjacent thereto there can further be printed symbols, codes or the like indication the type of product, size, absorption capacity or the like.

DESCRIPTION OF THE DRAWINGS

The invention will in the following be closer described with reference to some embodiments shown in the accompanying drawings.

DESCRIPTION OF EMBODIMENTS

Figure 1:
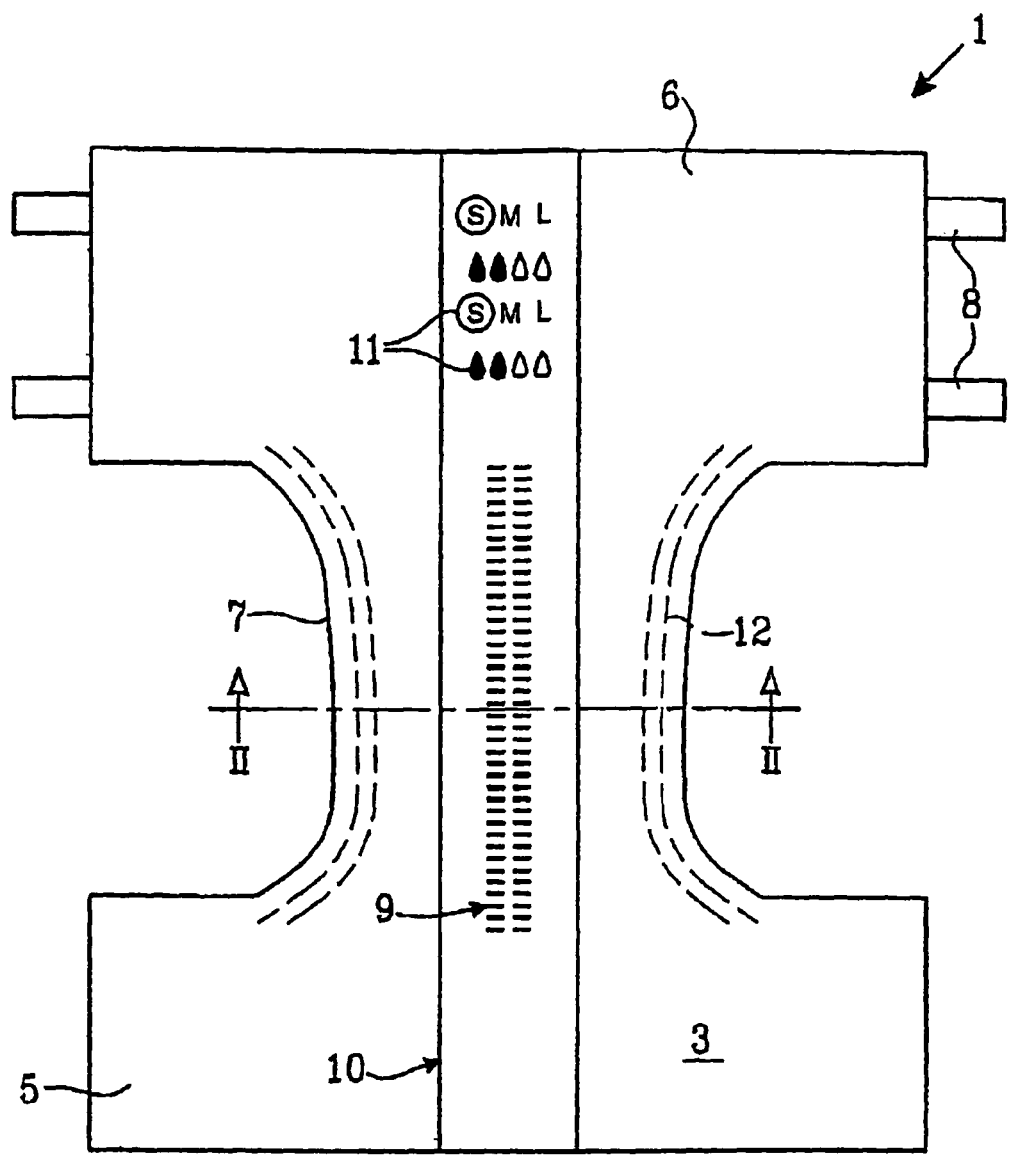
FIG. 1 is a plan view of a first embodiment of a diaper seen from the underside.
Figure 2:
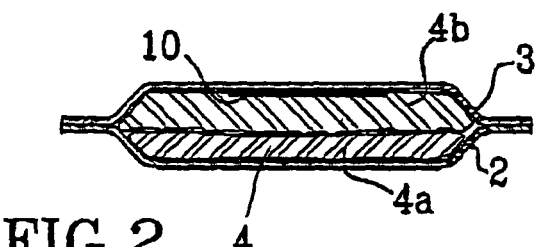
FIG. 2 is a section according to the line II-II in FIG. 1.

In FIGS. 1 and 2 there is disclosed an embodiment of a diaper 1, comprising a liquid pervious topsheet 2, a liquid impervious backsheet 3 and an absorbent body 4 enclosed therebetween. The absorbent body 4 can comprise two or more layers, such as liquid acquisition layer 4a and storage layer 4b.

The liquid pervious topsheet 2 can be a nonwoven material, for example a spunbond material of synthetic filaments, a meltblown material, a thermobonded material or a bonded carded fibrous web.

The liquid impervious backsheet material 3 can consist of a plastic film, a nonwoven material coated with a liquid impervious material or a hydrophobic nonwoven material which resists liquid penetration. The backsheet material can be a so called breathable material, which allows penetration of water vapour but prevents passage of liquid penetration. It may in this case be a porous plastic film, a nonwoven material or a laminate of a porous plastic film and a nonwoven material.

The topsheet 2 and the backsheet 3 have a somewhat larger extension in the plane than the absorbent body 4 and extend outside the edges thereof. The layers 2 and 3 are connected within their projecting portions, for example by gluing or welding with ultra sonic or heat.

The absorbent body 4 can be of any conventional kind. Examples of commonly occurring absorption materials are cellulosic fluff pulp, tissue layers, highly absorbent polymers (so called superabsorbents), absorbent foam materials, absorbent nonwoven materials and the like. It is common to combine cellulosic fluff pulp with superabsorbents in an absorbent body. It is also common to have absorbent bodies comprising layers of different materials with different properties with respect to liquid acquisition capacity, distribution capacity and storage capacity. This is well-known to the person skilled in the art and need therefor not be described in detail. The thin absorbent bodies that are common in for example baby diapers and incontinence guards often comprise a liquid storage layer 4b in the form of a compressed mixed or layered structure of cellulosic fluff pulp and superabsorbent and a liquid acquisition layer 4a arranged on top of the liquid storage layer, said liquid acquisition layer having an open porous structure with the ability to quickly acquire the discharged body fluid and temporarily store it before it is absorbed by the underlying storage layer 4b.

The diaper/incontinence guard is intended to enclose the lower part of the wearer's torso as a pair of absorbent pants. It is provided with a front portion 5 intended during use to be turned forwards on the user, and a rear portion 6 intended during use to be turned backwards on the user, and a narrower crotch portion 7 located between the front and rear portion, said crotch portion is intended to be applied in the crotch of the wearer between the legs. The rear portion 6 is provided with a pair of tape flaps 8 or other type of fastening means such as hook and loop type, and which are intended to be used for fasten together the diaper to the desired pantlike shape, Alternatively the fastening means can be arranged at the front portion. Around the leg portions there are arranged elastic threads 12 or the like, which provide a sealing effect around the thighs of the wearer.

Figure 4:
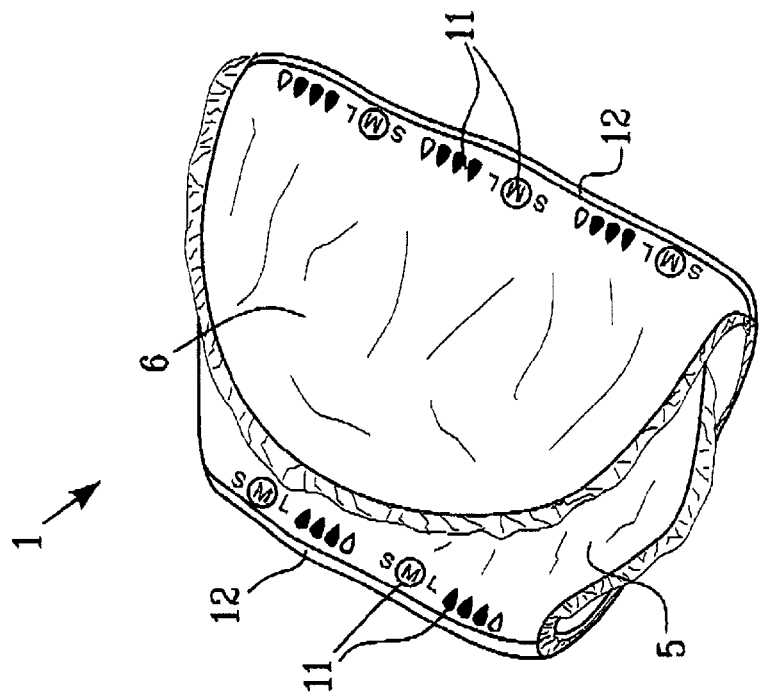
FIG. 4 shows in perspective a diaper in folded condition.
Figure 3:
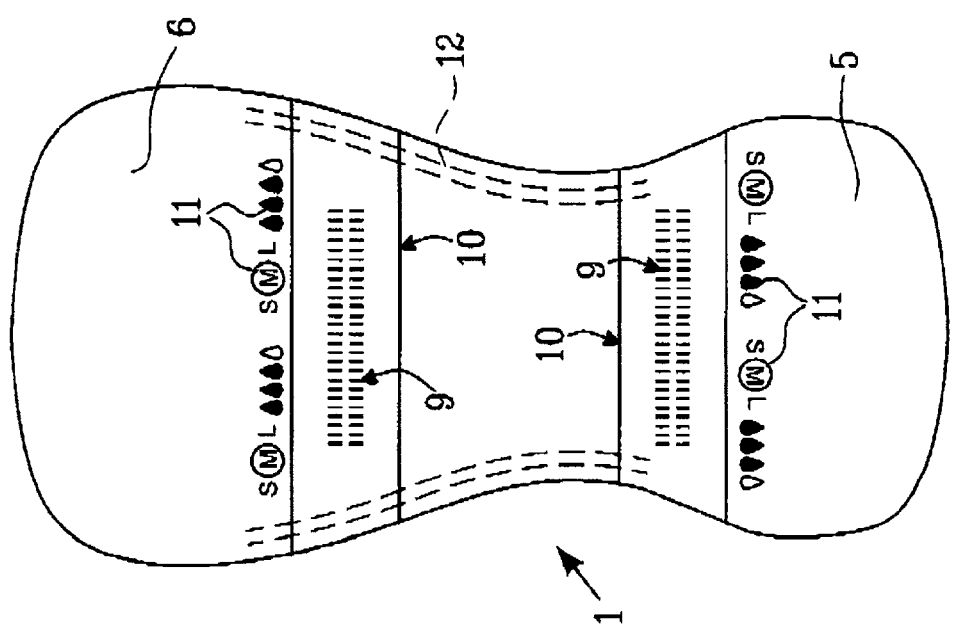
FIG. 3 is a plan view of another embodiment of an incontinence guard seen from the back side.
Figure 5:
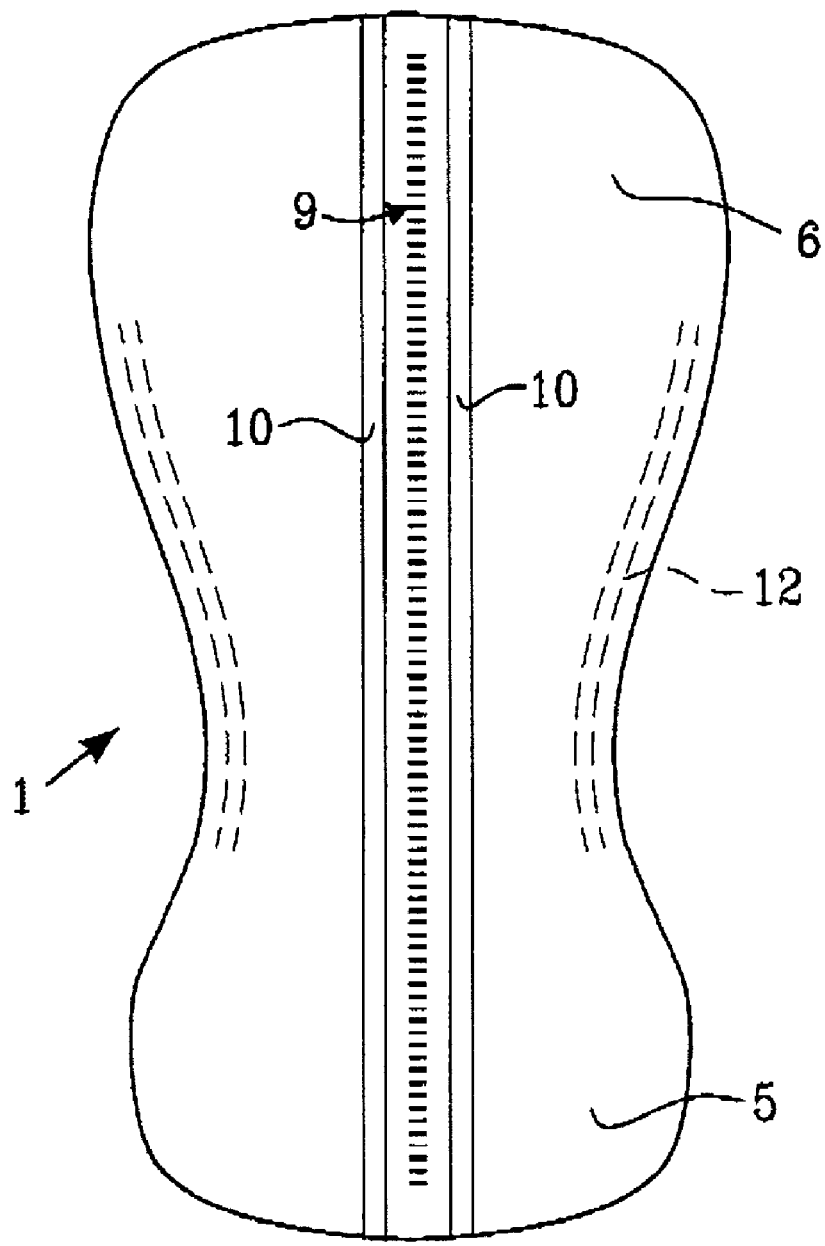
FIG. 5 is a plan view of a further embodiment of an incontinence guard seen from the backside.

In FIGS. 3-5 there are shown examples of an incontinence guard intended to be kept in place by a pair of tight pants. The fastening means in the form of rapes or hooks and loops are therefore lacking. Possibly there can on the underside of the backsheet material be applied glue strings or another kind of friction increasing means in order to keep the incontinence guard in place in the pants.

It is pointed out that the incontinence guard and the diaper shown in the drawings and described above only represent a couple of examples of absorbent articles and are by no means limiting for the present invention. Thus the shape of the article as well as its overall design can be varied. The absorbent article can also be a pant diaper, a belt-provided diaper or the like.

On the inside of the backsheet material 3 there is applied a wetness indicator 9, which preferably consists of a dyestuff which dissolves or changes colour or tint when brought into contact with liquid, and which is printed directly on the backsheet material or alternatively on a separate strip that is fastened to the inside of the backsheet material.

The wetness indicator 9 is applied on or adjacent at least one strip 10 with a colour or tint that is different the rest of the backsheet material. The strip 10 either consists of a part that is separate from the backsheet material 3 and is fastened to the inside thereof, or consists of a part of the backsheet material that is coloured in another colour or tint than the rest of the backsheet material. The strip 10 can consist of one single coloured strip or of a striped pattern or other optional pattern. The strip 10 may either be a continuous strip or may consist of several discontinuous portions arranged so as to form a discontinuous line. The strip 10 may also comprise two or more strips arranged close to each other.

In the embodiments shown in FIGS. 1-4 the wetness indicator 9 is applied on the strip 10, while in the embodiment shown in FIG. 5 it is applied between two strips 10 extending substantially in parallel.

According to a further embodiment the wetness indicator 9 may be visible through apertures or windows arranged in the strip 10.

By the fact that the wetness indicator 9 is applied on or adjacent such a strip 10, which has an appearance different from the rest of the backsheet material 3, the identification of the location of the wetness indicator 9 is facilitated. Moreover the colour, tint or other appearance of the strip 10, may be an indicator of the product type, size, absorption capacity or the like. On or adjacent the strip 10 there can be further arranged symbols 11, codes or the like, which indicate the product type, size, absorption capacity or the like. By this it is easier for the nurse to find the correct type of product in the case where the articles have been taken out of their packages and placed on a shelf or the like in a storage space in a nursing home or the like.

Besides the strip 10 may also serve as an indicator of the longitudinal centre of the article so that it is easier to put on the article correctly. It may also act as a longitudinal centre indicator during the manufacturing process.

The strip 10 can extend in the longitudinal direction of the article, preferably centrally along the product, as is shown in FIG. 1. It is also possible that the snip 10 extends in the transverse direction of The article, as is shown in FIGS. 3 and 4. In this case the strip 10 should be arranged at the part of the product intended to form a folding line 11 in th folded package condition of the article (see FIG. 4) In the case where the article is folded along two folding line there should be strips 10 at each folding line 11, so that independently of how the article is put on the shelf on strip 10 should be visible outwards.

The width of the strip 10 should be between 1 and 8 cm, preferably between 2 and 7 cm and more preferably between 3 and 6 cm.

The invention is of course not limited to the described and illustrated embodiments but a plurality of modifications are possible within the scope of the claims.

The invention claimed is:

1. An absorbent article comprising:
   a liquid pervious topsheet,
   a liquid impervious backsheet,
   an absorbent body enclosed therebetween,
   the liquid-impervious backsheet comprising a strip part and a remaining part, the strip part being an integral part of the backsheet, the strip part having a different color than the remaining part of the backsheet, and
   a wetness indicator arranged at an inside of the liquid impervious backsheet in a pattern and being visible through the backsheet,
   wherein the wetness indicator is disposed on or adjacent to the strip part such that identification of the location of the wetness indicator on or adjacent to the strip part is facilitated by the strip part that has a color and wherein that color is different than the color of the remaining part of the backsheet,
   wherein the strip part has a width of between 1 and 6 cm, and wherein the color of the strip part is an indicia that provides an indication of size, or absorption capacity of the article.

2. The absorbent article as claimed in claim 1, the article having a length in a longitudinal direction, the strip part extending in the longitudinal direction of the article over an entire length or at least an essential part of the length of the article.

3. The absorbent article as claimed in claim 1, wherein the strip part extends in a transverse direction of the article and is applied at a part of the article that is intended to form a folding line for a folded packaging position of the article.

4. The absorbent article as claimed in claim 1, wherein the strip part has a width between 1 and 8 cm.

5. The absorbent article as claimed in claim 1, further comprising:
printed symbols or codes on or adjacent the strip part, the printed symbols or codes also being an indication of a product type, size, or absorption capacity of the article.

6. An absorbent article as claimed in claim 1, wherein the absorbent article is a diaper or an incontinence guard.

7. The absorbent article as claimed in claim 1, wherein the strip part is between 2 and 7 cm in width.

8. The absorbent article as claimed in claim 1, wherein the strip part is between 3 and 6 cm in width.

9. The absorbent article as claimed in claim 1, wherein the wetness indicator is disposed on the strip part such that identification of the location of the wetness indicator on the strip part is facilitated by the strip part that has a color and wherein that color is different than the color of the remaining part of the backsheet.

10. An absorbent article comprising:
a liquid pervious topsheet;
a liquid impervious backsheet;
an absorbent body enclosed therebetween;
a separate strip of material fastened on the inside of the backsheet, the strip having a different color than the backsheet; and
a plurality of wetness indicators arranged at an inside of the liquid impervious backsheet in a pattern and being visible through the backsheet,
wherein the wetness indicators are disposed on or adjacent to the strip such that identification of the location of the plurality of wetness indicators on or adjacent to the strip is facilitated by the strip that has a color and wherein that color is different than the color of the remaining part of the backsheet,
wherein the strip has a width of between 1 and 6 cm, and
wherein the color of the strip is an indicia that provides an indication of size, or absorption capacity of the article.

11. The absorbent article as claimed in claim 10, the article having a length in a longitudinal direction, the strip extending in the longitudinal direction of the article over an entire length or at least an essential part of the length of the article.

12. The absorbent article as claimed in claim 10, wherein the strip extends in a transverse direction of the article and is applied at a part of the article that is intended to form a folding line for a folded packaging position of the article.

13. The absorbent article as claimed in claim 10, wherein the strip has a width between 1 and 8 cm.

14. The absorbent article as claimed in claim 10, further comprising:
printed symbols or codes on or adjacent the strip, the printed symbols or codes also being an indication of a product type, size, or absorption capacity of the article.

15. An absorbent article as claimed in claim 10, wherein the absorbent article is a diaper or an incontinence guard.

16. The absorbent article as claimed in claim 10, wherein the strip is between 2 and 7 cm in width.

17. The absorbent article as claimed in claim 10, wherein the strip is between 3 and 6 cm in width.

18. The absorbent article as claimed in claim 10, wherein the wetness indicators are disposed on the strip such that identification of the location of the plurality of wetness indicators on the strip is facilitated by the strip that has a color and wherein that color is different than the color of the remaining part of the backsheet.

19. An assortment of products comprising:
a plurality of absorbent articles of at least two different sizes, or absorption capacities of the articles,
wherein each absorbent article comprises:
a liquid pervious topsheet,
a liquid impervious backsheet,
an absorbent body enclosed therebetween,
the liquid-impervious backsheet comprising a strip part and a remaining part, the strip part being an integral part of the backsheet, the strip part having a different color than the remaining part of the backsheet, and
a wetness indicator arranged at an inside of the liquid impervious backsheet in a pattern and being visible through the backsheet,
wherein the wetness indicator is disposed on or adjacent to the strip part such that identification of the location of the wetness indicator on or adjacent to the strip part is facilitated by the strip part that has a color and wherein that color is different than the color of the remaining part of the backsheet,
wherein the strip part has a width of between 1 and 6 cm, and
wherein different colors of the strip part are an indicia that provides an indication of the difference in the size, or absorption capacity of the article.

20. An assortment of products comprising:
a plurality of absorbent articles of at least two different sizes, or absorption capacities of the articles,
wherein each absorbent article comprises:
a liquid pervious topsheet;
a liquid impervious backsheet;
an absorbent body enclosed therebetween;
a separate strip of material fastened on the inside of the backsheet, the strip having a different color than the backsheet; and
a plurality of wetness indicators arranged at an inside of the liquid impervious backsheet in a pattern and being visible through the backsheet,
wherein the wetness indicators are disposed on or adjacent to the strip such that identification of the location of the plurality of wetness indicators on or adjacent to the strip is facilitated by the strip that has a color and wherein that color is different than the color of the remaining part of the backsheet,
wherein the strip has a width of between 1 and 6 cm, and
wherein different colors of the strip are an indicia that provides an indication of the difference in the size, or absorption capacity of the article.

* * * * *